United States Patent [19]
Katz et al.

[11] Patent Number: 5,786,207
[45] Date of Patent: Jul. 28, 1998

[54] TISSUE DISSOCIATING SYSTEM AND METHOD

[75] Inventors: Adam J. Katz; Ramon Llull, both of Pittsburgh, Pa.

[73] Assignee: University of Pittsburgh, Pittsburgh, Pa.

[21] Appl. No.: 864,444

[22] Filed: May 28, 1997

[51] Int. Cl.$^6$ .................................................. C07G 17/00
[52] U.S. Cl. .................. 435/267; 435/271; 435/283.1; 435/297.1; 435/298.2; 435/308.1
[58] Field of Search .................................. 435/262, 267, 435/271, 283.1, 297.1, 298.2, 308.1; 494/36

[56] References Cited

U.S. PATENT DOCUMENTS

| | | | |
|---|---|---|---|
| 5,035,708 | 7/1991 | Alchas et al. | 623/1 |
| 5,330,914 | 7/1994 | Uhlen et al. | 435/270 |
| 5,372,945 | 12/1994 | Alchas et al. | 435/267 |
| 5,409,833 | 4/1995 | Hu et al. | 435/1 |
| 5,610,074 | 3/1997 | Beritashvili et al. | 436/177 |

Primary Examiner—David A. Redding
Attorney, Agent, or Firm—Titus & McConomy

[57] ABSTRACT

A tissue dissociation method and system for washing and dissociating tissue and producing a cellular suspension for use in autologous, cell-based therapies or research wherein a sterile environment is maintained. More particularly, a system for dissociating tissue comprising a housing unit, a first compartment having a plurality of pores providing for fluid communication between the interior of the first compartment and the interior of the housing unit, a first inlet port that provides communication between the exterior environment and the interior of the first compartment and thereby provides a means for introducing solutions into the interior of the first compartment, a second compartment, a second inlet port for introducing a tissue sample into the system, a means for agitating or rotating the second compartment in the housing unit, a means for controlling the exit of effluent from the housing unit, a first receptacle, and a centrifuge-ready second receptacle for collecting a resulting cell suspension. The method comprises introducing a tissue sample into the system and subjecting it to a washing phase and a dissociating phase wherein the tissue is agitated or rotated. The tissue may also be subjected to a sedentary phase and a phase in which a solution is added to the resulting cell suspension to cease tissue dissociation. At the conclusion of the tissue dissociation process, the resulting cell suspension is collected in a centrifuge-ready receptacle.

20 Claims, 4 Drawing Sheets

1

TISSUE DISSOCIATING SYSTEM AND METHOD

FIELD OF THE INVENTION

The present invention relates to a method and a system for dissociating tissue and separating cells therefrom. In particular, the present invention relates to a method and system for dissociating adipose tissue and separating cells therefrom.

BACKGROUND OF THE INVENTION

The burgeoning field of tissue engineering embodies the frontier of medical technology. A particularly exciting area of tissue engineering is the emerging technology of "self-cell" therapy whereby autologous cells of a given tissue type are removed from a patient, isolated, mitotically expanded, perhaps genetically engineered, and ultimately reintroduced to the donor/patient with or without synthetic materials/matrices. One goal of self-cell therapy is to help guide and direct the rapid and specific repair or regeneration of tissues. Another goal of self-cell therapy is to introduce a "neo-organ" which functions to produce a missing or inadequate amount of a biologically active substance. Such self-cell therapy is already a part of clinical practice. See e.g., autologous bone marrow transplants for various hematologic conditions. The rapid advancement of this technological paradigm further is reflected in recent publications which disclose rapid progress towards bone and cartilage self-cell therapy. Similar advances are being made with other tissues such as muscle, liver, pancreas, tendon and ligament. One of the greatest advantages of self-cell therapy over current technologies is that the autologous nature of the tissue/cells greatly reduces, if not eliminates, immunological rejection and associated costs. Thus, current organ, tissue and biological materials shortages may no longer limit treatment modalities.

One form of of self-cell therapy that recently has received increased attention is based on the use of adipose tissue. Such adipose tissue based therapy and the corresponding technologies have gained attention for a variety of reasons. First, adipose tissue is abundant in most human beings and the vast majority of humans have enough subcutaneous adipose tissue to donate the amount required for self-cell therapy without any significant biological or anatomical consequences. Second, adipose tissue is easily obtained. It may often be obtained through liposuction, the most performed aesthetic operation in the world. Liposuction is a minimally invasive procedure and when combined with subcutaneous infiltration of anesthetic solution, can be performed with the patient awake or sedated.

Various liposuction techniques exist including ultrasonic-assisted liposuction ("UAL"), laser-assisted liposuction, and traditional suction-assisted liposuction ("SAL") wherein the fat is removed with the assistance of a vacuum created by either a mechanical source or a syringe, e.g., a Tulip Syringe.™ Each of the foregoing liposuction techniques may be used in conjunction with tumescent solution. Liposuction procedures that use the tumescent technique involve the pre-operative infiltration of subcutaneous adipose tissue with frequently large volumes of dilute anesthetic solutions. The tumescent solution generally is comprised of saline or Ringers' solution containing low doses of epinephrine and lidocaine (e.g.,0.025%–0.1% of the saline or Ringer's solution). The amount of tumescent solution infiltrated is variable, but typically is in ratios of 2 to 3 cc of infiltrate per 1 cc of aspirated adipose tissue. Some practitioners use tissue turgor as the endpoint for tumescent solution infiltration. See Rohrich et al., "Role of Subcutaneous Infiltration in Suction-Assisted Lipoplasty: A Review," Plastic and Reconstructive Surgery, 99:514–519 (Feb. 1997), included by reference herein, for a description of liposuctioning techniques, including techniques performed with tumescent solution. The evolution of the tumescent technique has revolutionized liposuction by making it safer and possible on an outpatient basis. Specifically, it makes the use of general anesthesia optional in most cases and thereby avoids the associated risks and costs. In addition, it significantly reduces the amount of blood lost while the fat is being harvested and thereby increases the amount of fat that can be removed during a liposuction procedure without the need for blood transfusions. In short, the use of tumescent solutions has become routine, regardless of the specific liposuction technique, e.g. UAL, laser-assisted or SAL, and is incorporated in most liposuction procedures.

In addition to being abundant and easy to procure, adipose tissue is a source of several different cell types including adipocytes, adipose precursor cells, fibroblasts and vascular endothelial cells. Further, adipose tissue is a potential source of extracellular matrix components, bioactive growth factors, paracrine and endocrine hormones, and perhaps even the progeny of mesenchymal stem cells at a developmental stage which still confers multipotent plasticity. For example, researchers are able to manipulate the growth and differentiation of adipocyte precursor cells derived from human adipose tissue. More specifically, researchers have been able to culture-expand adipose precursor cells harvested from human liposuction tissue and to chemically stimulate the terminal differentiation of such cells. Furthermore, it is possible to de-differentiate mature terminally differentiated adipocytes, culture-expand such cells, and re-differentiate those cells.

The process used by researchers to dissociate tissue and separate and isolate cells from a tissue sample is tedious, time consuming, labor intensive, subject to contamination, and generally limited to the laboratory setting. The procedure relating to tissue dissociation and cell separation is fundamentally the same and always required irrespective of the starting tissue sample or specific cell population(s) to be isolated (hereinafter, "tissue dissociation," which is a macro form of cell separation, is used interchangeably with the term "cell separation"). Cell separation is always a prerequisite and often the rate-limiting step of cell isolation. Cell isolation, in turn, is necessary for the development, evaluation and application of all self-cell therapies derived from intact tissues. Because much of tissue engineering depends on cell harvest and cell isolation, cell separation is essential for the generation and application of self-cell therapies.

Current methods for cell separation require specialized laboratory space and skilled personnel. In contrast, the present invention can be used in a variety of settings without special training.

Several devices exist for the isolation of certain cells. For example, U.S. Pat. Nos. 5,035,708 and 5,372,945 issued to Alchas et al. describe an endothelial cell procurement and deposition kit and a device and method for collecting and processing fat tissue and procuring microvessel endothelial cells to produce endothelial cell products. Further, U.S. Pat. No. 5,409,833 issued to Hu et al. discloses a microvessel cell isolation apparatus. Unlike the present invention, however, each of these inventions has limited utility because they are directed only toward the isolation of microvessel endothelial cells and the transplantation of such cells onto the surface of synthetic vascular grafts. In contrast, the present invention may be used to isolate a variety of tissue types and sizes. Further, each of these inventions is exceptionally complex relative to the present invention and therefore more expensive to manufacture. Thus, in contrast to existing devices, which are directed towards limited applications, the present invention is simpler, more versatile, and will provide convenient availability.

Finally, the volume and consistency of adipose tissue harvested through liposuction presents several unique challenges in the creation of a cell suspension. For example, the volume of tissue generated by liposuction is much larger than the volume of most tissues subjected to tissue dissociation or cell separation processes. Further, the tumescent solutions used in conjunction with most liposuction procedures significantly increase the original adipose tissue sample volume. The viscosity of the tissue sample is further increased by the oil released from cells damaged during the liposuction procedure or cell separation process. Thus, one of the most difficult aspects of processing liposuctioned adipose tissue, particularly adipose tissue that is removed with a tumescent solution, is its thick, slurry-like consistency which is caused by oil, serum, tissue fragments and other fluids. The consistency of such liposuctioned tissue, particularly large samples of such tissue, causes occlusion of filtering mechanisms and is a significant hindrance to thorough, effective washing and cell separation.

None of the devices disclosed above addresses the special processing concerns presented by working with large volumes of tissue in general or the particular problems of working with adipose tissue subjected to tumescent solutions. Thus, although various techniques and devices for cell separation are well documented in the literature, a need exists for a device and method that is more expeditious, efficacious, accessible and practical than current devices and methods. Further, a need exists for a device and method that overcomes the unique challenges presented by cell separation from adipose tissue.

SUMMARY OF THE INVENTION

The present invention consists of a housing unit that possesses a means for providing access to its interior space for facile cleaning, substitution and maintenance of the system's components. Such access may be accomplished through a hinging or threading mechanism on the housing unit. When the mechanism for providing access to the interior of the housing unit is in the closed position, an airtight and waterproof seal is formed around the access points. The base of the housing unit is beveled or frusto-conical in shape to create a funnel which directs aqueous solutions to an aperture in the base of the housing unit. The grade of the funnel is selected such that it provides for relatively fast removal of effluent from the housing unit when the aperture is open, but when the aperture is closed and solution is introduced into the housing unit, the depth of the funnel ensures that substantially all the fluid collected in the funnel is employed in interacting with tissue contained in a second compartment. Whether this aperture is closed, open, spanned by a filter, or open or filtered with the application of a vacuum, depends on the positioning of a valve or other mechanism that controls the exit aperture. External to the housing unit and in direct or indirect communication with the aperture in the base of the housing unit, is a mechanism for attaching receptacles to receive effluent from the housing system. When receptacles are attached to the housing unit, either directly or indirectly, the mechanism of interaction between the housing unit and the receptacles creates a sterile system for the tissue dissociation process. Such receptacles are used to collect effluent, generally discarded as waste, and cell suspensions resulting from the cell separation process. The receptacle components, including whatever device or component that is part of or attached to the receptacle components to prevent fluid loss and maintain a sterile environment after disengagement from the housing unit, e.g. a cap, are sterile, disposable, and immediately usable in standard centrifuges without adaptation.

Two compartments exist in the housing unit. The first compartment, which is superiorly positioned in the housing unit relative to the second compartment, provides for the storage and dispensation of washing solutions, and possibly digestion and other solutions, into the housing unit and onto and into the chamber of the second compartment. The first compartment possesses at least one port that provides for communication between the exterior environment and the interior of the first compartment and sterile introduction of solutions used during the cell separation process. The port(s) of the first compartment, like other ports of the present invention, is able or adaptable to accept commercially-available syringe tips, stopcocks, sterile syringe filters, or any combination thereof. Preferably such ports are self-sealing when such devices are not attached thereto, and when such devices are attached thereto, they are sealably engaged with the port. The first compartment possesses openings on at least the surface that faces the chamber of the second compartment to enable fluids inserted in the first compartment to diffuse from inside the first compartment into the housing unit, onto the exterior surface of the chamber of the second compartment, pass through the partition that defines the second compartment, and interact with tissue(s) which have been inserted therein. Preferably, the first compartment is positioned directly over the second compartment.

The second compartment of the present invention is a removable filtering device chosen for its optimal pore size and material composition for washing and dissociating a given tissue specimen. Accordingly, the pore size of the second compartment will vary depending on the tissue type, although generally such pore size will be in the range of approximately 50–2000 micrometers. The internal volume of the filtering device employed in the system also depends on the characteristics and size of the tissue specimen to be processed, although preferably the second compartment will substantially fill the interior of the housing unit. The filtering device has dowels at opposing ends that interact with annuli presented by the housing unit. These filtering device dowels provide a means for securing the filtering device in the housing unit while the filtering device is rotated or agitated, and also provide for facile interchange of filtering devices of different volumes and pore sizes so that the most efficient filtering device may be used in the system for a given tissue type or size. Preferably, the filtering device is positioned within the housing unit so as to most efficiently consume the interior of the housing unit, interact with the functioning of the first compartment, and provide easy insertion and removal of the second compartment. Radiating out from and extending from the external surface of the filtering device are intermittently spaced extensions. Through either agitation or full or partial revolution of the filtering device, these extensions mix fluid present in the housing unit. Such mixing is important for the enzymatic digestion step because it optimizes the surface area of tissue interacting with the digestive enzymes and facilitates and accelerates the enzymatic interaction. The sporadic and preferably perpendicular arrangement of these extensions provides for de minimis interference of fluid exchange between the interior of the second compartment and the interior of the housing unit.

As noted above, the extreme ends of the second compartment have dowels that provide a means for engaging the second compartment with the housing unit in a secure manner and provide for facile substitution of other filtering devices. The housing unit has a corresponding means for engaging the dowels of the second compartment. At least one dowel of the second compartment is hollow and forms a port to provide a sterile means for injecting tissue samples and solutions into the interior cavity of the second compartment. Further, the housing unit has an aperture at the point of connection between the second compartment dowels serving as a port and the means for engaging the dowels of the second compartment in the housing unit. Thus, when the second compartment is secured in the housing unit, the port of the second compartment is aligned with and extends through an annuli encircling an aperture on the wall of the housing unit. The aperture in the housing unit accommodating the dowel of the second compartment is further lined with an elastomeric material that creates an airtight and watertight seal when the projection of the second compartment is engaged therein. Accordingly, the port of the second compartment extends through the wall of the housing unit, allows communication between the interior of the second compartment and the external environment, and provides a means for inserting tissue samples, and possibly solutions, into the system. The second compartment port is self-sealing and provides a sterile mechanism for introducing solutions and tissue samples into the interior of the second compartment. This configuration of the second compartment port provides a sterile internal environment and a portal of entry for the sterile introduction of tissue specimens and solutions.

At least one dowel of the second compartment provides a means for either manual or automated rotation or agitation of the second compartment from an external source.

The housing unit also possesses at least one filtered port that provides a means of communication between the interior of the housing unit and external environment and permits filtered air to flow into the interior of the housing unit to facilitate the maintenance of atmospheric pressure. Such port is located in the upper portion of the housing unit such that if sufficient fluid were introduced into the system to submerge the second compartment, such port would be above the fluid line.

Connected to the aperture in the base of the housing unit is a valve that controls egress of the effluent from the housing unit into receptacles attached directly or indirectly to the housing unit. The valve has at least two positions, closed and open. In the closed position, an airtight and watertight seal prevents fluid in the housing unit from passing through the exit aperture. In the open position, effluent may pass from the housing unit into a receptacle external to the housing unit. The valve may also have an open position with a filter spanning the exit aperture. As noted above, the exterior of the housing unit, or the valve controlling the status of the exit aperture, has a means for attaching collection receptacles and/or filtering devices in alignment with the exit aperture of the housing unit. In some embodiments, a vacuum is applied to assist the flow of effluent. In some embodiments of the invention, a probe is inserted into the housing unit to measure the reactions occurring therein.

Finally, the system preferably possesses a heat source, providing a means for heating the dissociation solution in the portion of the housing unit enclosing the second compartment. When the heat source is activated, it substantially brings the dissociation solution to and maintains it at an optimal temperature for enzymatic dissociation for the tissue and enzyme chosen.

The following describes a method of processing tissue using the system described above. First, the filtering device, chosen for its suitability for the tissue type and size, is positioned in the annuli of the housing unit and a sterile first collection receptacle is attached, either directly or indirectly, to the housing unit in alignment with the exit aperture. A sterile environment is created by engaging the sealing mechanisms of the housing unit and occluding the aperture in the base of the housing unit.

A tissue sample is introduced into the second compartment/filtering device via a second compartment port which extends through an aperture in the housing unit. Depending on the properties of the tissue sample, the tissue sample may be subjected to a sedentary phase in which the sample resides in the second compartment for an interval and components of the tissue sample separate out based on their properties. Such a sedentary phase would be warranted only if the bottom layer resulting from such separation was a component whose separation from other tissue components did not require enzymatic dissociation. If the sample is subjected to a sedentary phase, the valve controlling the exit aperture is placed in the open position and the lower layer resulting from such sedentary phase is permitted to pass through the pores of the second compartment, through the exit aperture, and into a collection receptacle. Tissues requiring dissociation are retained in the second compartment.

Subsequent to a possible sedentary phase, the tissue sample is subjected to a washing phase. The washing solution used in the system, like the digesting and other solutions described herein, is selected for its specificity for the tissue from which cells are to be separated. The washing solution, which may be comprised of a sterile buffered rinsing solution such as PBS, Hank's Balanced Salt Solution, or a tissue-specific media, is inserted into the first compartment through a port providing access to the interior of the first compartment, preferably under pressurized conditions. The washing solution exudes through the pores of the first compartment into the housing unit and onto and into the second compartment through the pores of the second compartment. Processing tissue samples that are large and/ or have a thick consistency has often caused occlusion of the screens or compartments used during the washing phase. The present invention overcomes this problem by two independent but synergistic mechanisms: (1) rotation or agitation of the second compartment and (2) application and interaction of the washing solution. Preferably, the second compartment is rotated, either manually or automatically, such that gravitational forces draw occluding material toward the interior of the second compartment, resulting in a "tumbling-like" effect which facilitates the tissue sample's exposure to the washing solution and deters occlusion of the pores of the second compartment. Preferably, sufficient washing solution is introduced into the system to substantially submerge the second compartment. The extensions of the second compartment further encourage interaction of the washing solution with the tissue sample. The combination of the revolving/agitating second compartment and washing solution descending from the superiorly positioned reservoir pores results in a more effective and efficient washing phase than devices or methods lacking such steps. After completion of the washing phase, as determined by gross macroscopic examination or based on previously-determined objective criteria, the valve controlling the exit aperture is placed in the open position thereby allowing for communication between the housing unit and the first collection receptacle via the exit aperture. The washing solution effluent exits the housing unit via the exit aperture and is collected in the sterile first collection receptacle. After completion of the washing phase and removal of the washing solution from the housing unit, the exit aperture is occluded. The first collection receptacle is disengaged from the housing unit and the effluent therein, often deemed to be waste, is handled appropriately. A sterile centrifuge-ready second receptacle is attached, either directly or indirectly, to the housing unit in alignment with the exit aperture. At the conclusion of this phase, a thoroughly washed tissue specimen exists in the second compartment.

Dissociation of the tissue sample is the next step in the process. A proteolytic enzymatic solution, selected for its specificity to the tissue to be digested, is introduced into the housing unit via a port that directly or indirectly provides access to the housing unit. Enough enzymatic solution is introduced into the housing unit to substantially submerge the tissue sample in the filtering device. The heat source is activated and set to maintain an internal fluid temperature for optimal enzymatic dissociation for the specific tissue and proteolytic enzyme.

During the tissue dissociation step, the second compartment is agitated or rotated, either manually or by a power motor, and extensions radiating out from the second compartment provide continuous, gentle mixing of the tissue/enzyme solution in the housing unit and accelerate the tissue dissociation process. After appropriate dissociation time, as determined based on macroscopic evaluation or previously determined objective criteria, the mechanism controlling the status of the exit aperture is adjusted such that the exit aperture is open and the cell suspension resulting from tissue dissociation is permitted to travel through the exit aperture into the sterile centrifuge-ready receptacle. Non-digested debris remains trapped in the second compartment.

Thus, the present invention concludes with the creation of a cell suspension which is delivered into a sterile centrifuge-ready container. Because most cell suspensions resulting from a cell separation process are heterogenous in composition (including unwanted debris), they typically require further processing, the details of which vary depending on the specific cell type(s) to be isolated. Often, such processing is merely a few additional centrifugation and/or filtration steps.

Several steps and features of the present invention may be automated, including programmably-automated. For example, with respect to solutions introduced into the system, the amounts of such fluid, the time over which they are delivered, and the pressure of such delivery duration. The duration of the sedentary, washing and dissociating phases may be automated. The movement of the second compartment, including whether such movement is agitation or rotation, its speed and duration, may also be automated. The positioning of the mechanism controlling the status of the exit aperture may be automated. In embodiments that provide for opening and closing the plurality of ports for the first compartment, the status of such ports may be automated. In embodiments of the invention that incorporate a probe in the housing unit to measure the reactions occurring therein, certain automated steps of the invention may rely on input from such probe.

It is an object of this invention to provide a more efficient, versatile, cost-effective, sterile method and system for dissociating tissue samples into a cell suspension.

It is also an object of the invention to provide a more efficient, cost-effective, sterile method and system that overcomes the deficiencies of prior devices and systems for the dissociation of adipose tissue for self-cell therapy.

It is a further object of the invention to provide a more sterile method and system that overcomes the unique challenges posed by processing large volumes of adipose tissue.

Another object of the invention is to provide a method and system that addresses the unique challenges and advantages of processing of adipose tissue harvested by liposuction using tumescent solution.

Other objects and advantages of the present invention will become apparent from perusing the following detailed description of presently preferred embodiments taken in conjunction with the accompanying drawings.

DETAILED DESCRIPTION OF PREFERRED EMBODIMENTS

Figure 1:
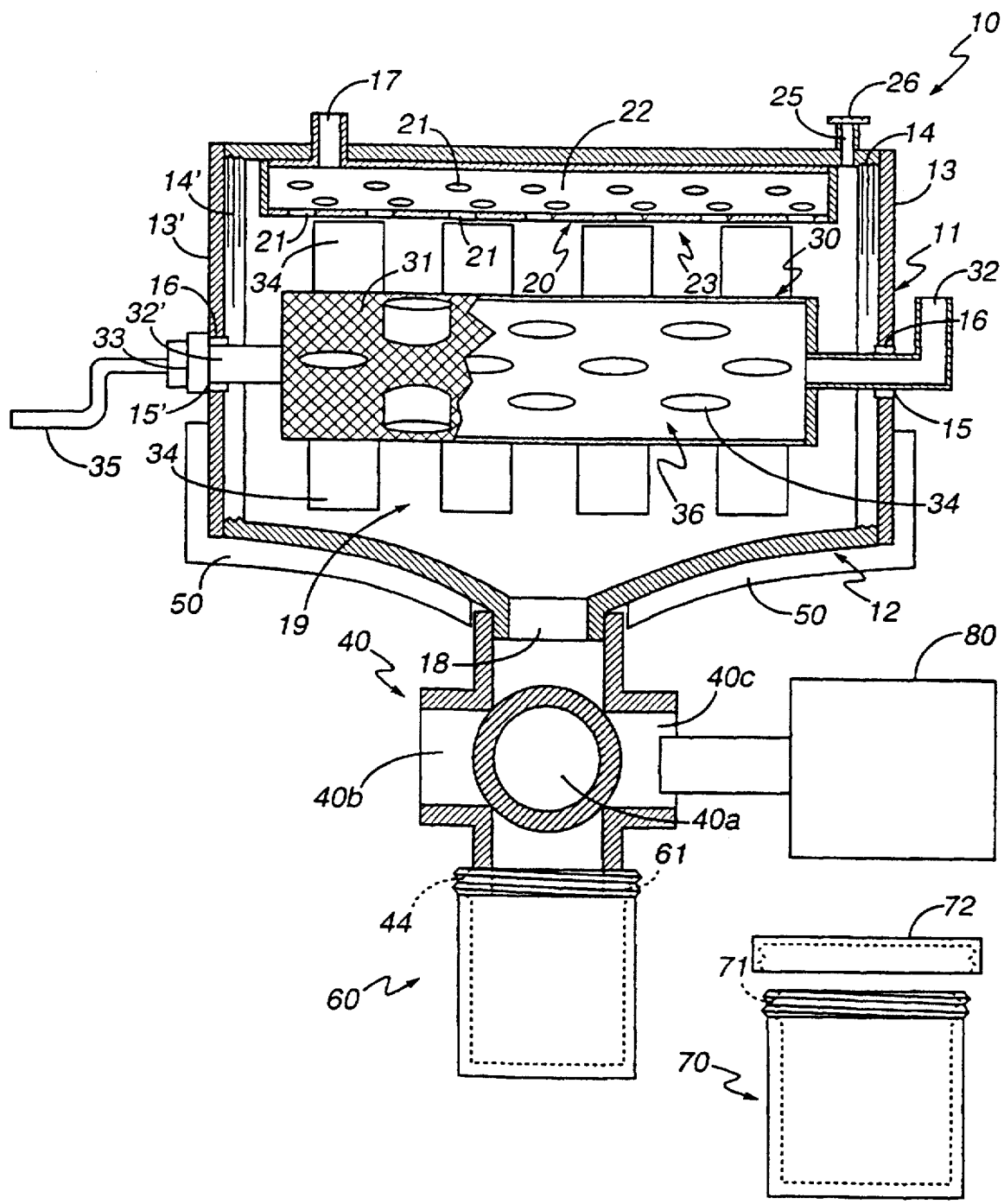
FIG. 1 is a cross sectional front view of a system embodying the present invention.
Figure 2:
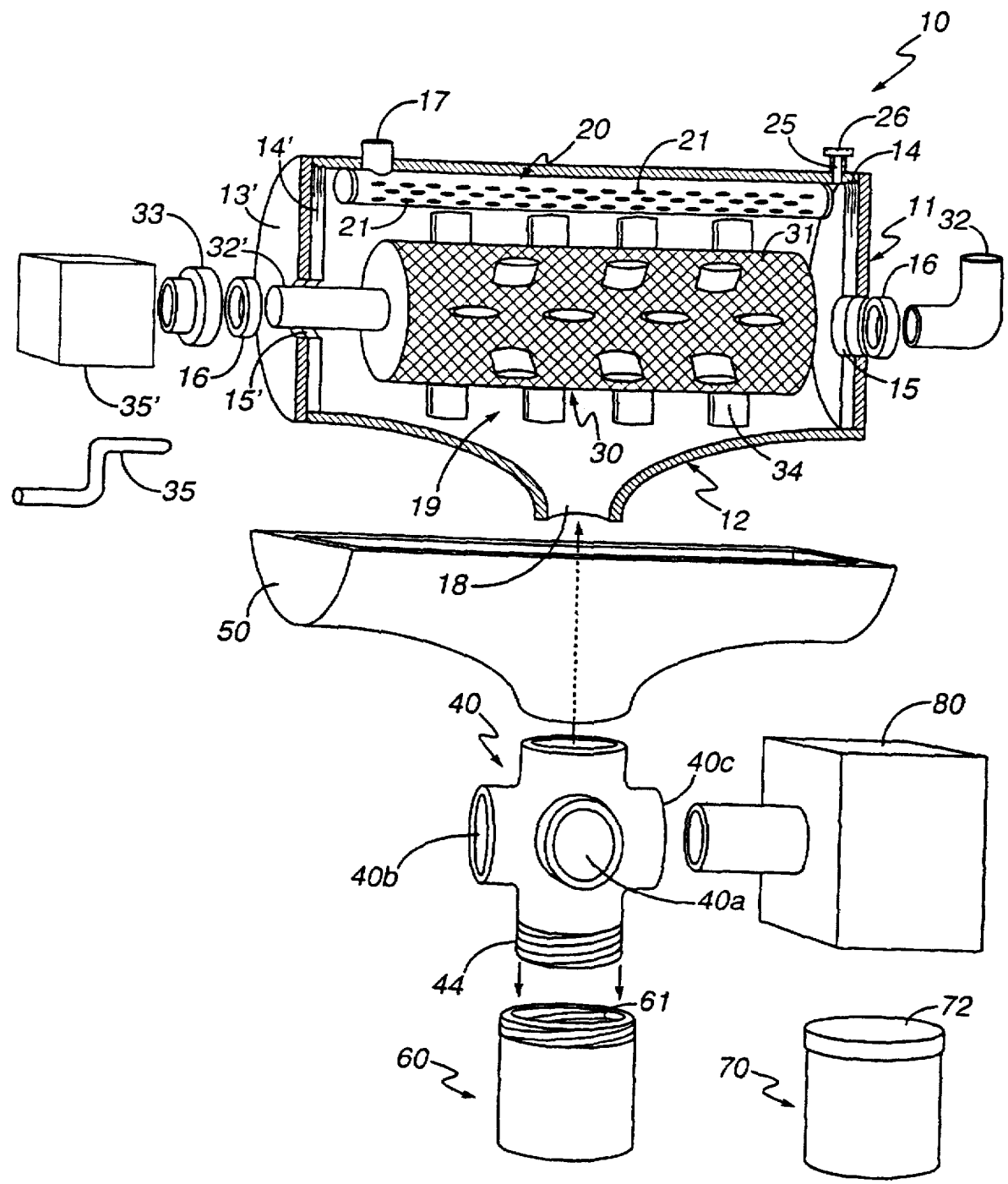
FIG. 2 is an oblique exploded perspective view of the system embodying the present invention depicted in FIG. 1

In a first embodiment of the invention, shown in FIGS. 1 and 2, the housing unit 10 has a first section 11 which is substantially cylindrical in shape and a second section 12 which is frusto-conical in shape. The housing unit 10 is constructed of an inexpensive material able to withstand the temperatures achieved during autoclave sterilization, e.g. 200°–300° F., or disposable materials. In a yet more preferred embodiment, the housing unit is constructed of a translucent material that permits visual observation of processes occurring in the housing unit. At least one of the discs 13, 13' which comprise the ends of the substantially cylindrical portion of the housing unit is removable to permit easy access to the interior of the housing unit. Preferably, each such removable disc has threads 14' which correspond to threads presented by the housing unit 14 and when such threads are mated, an airtight and watertight seal is formed by such threads. Further, annuli 15, 15' exist in such discs 13, 13' which provide a means for securing a second compartment 30 inside the housing unit.

A first port 17 exists in the housing unit that provides for communication between the interior of a first compartment 20 located therein and the external environment and thereby provides a means for inserting various fluids, e.g., washing and digesting fluids, into the first compartment. Preferably, such first port is self-sealing such that when a fluid source is not engaged with the first port, the first port is closed with an airtight and watertight seal. A second port 25 having a filter 26 that spans its opening, exists in the housing unit which provides a means of communication between the interior of the housing unit 19 and external environment and permits filtered air to flow into the interior of the housing unit. Such port is located in the upper portion of the housing unit such that when sufficient fluids are introduced into the system to submerge the second compartment, such port is above the fluid line.

The base 12 of the housing unit is substantially frusto-conical in shape. At the apex of such frusto-conical shape is an exit aperture 18. The status of the exit aperture is controlled by a valve 40 having at least two positions, open 40a and closed 40b. In one preferred embodiment, the valve possesses a third position 40c which is a variation of the open position and provides for the attachment of a vacuum 80 to facilitate and accelerate removal of effluent from the housing unit. Accordingly, in one preferred embodiment, the valve is a three-way valve attached to the housing unit. The three-way valve has a first closed position 40b, a second open position 40a, and a third open position with a vacuum 40c. In one embodiment, the valve is a three-way stopcock valve.

Attached to or part of the three-way valve is a means for sealably attaching a receptacle to collect effluent passing through the exit aperture and three-way valve configuration. In one embodiment, the three-way valve has an exterior lip that is threaded 44 to provide a means for attaching and sealably engaging thereto receptacles 60, 70 having complementary threads 61, 71. In another embodiment, male-female thread adapters are appended to the valve to facilitate the use of a wide range of receptacle sizes and shapes which can accommodate varying effluent volumes. Other embodiments include inserting a filter between the exit aperture and the sealably attached collection receptacle.

The first compartment 20, which may be permanently or temporarily secured in the housing unit, is comprised of tubing having a plurality of ports 21 allowing fluid communication between the interior of the first compartment 22 and the interior of the housing unit 19. Such ports are in addition to the port 17 providing for communication between the interior of the first compartment and the external environment. Preferably, such ports 21 are located on a substantial area of the surface of the first compartment directed towards the second compartment 23 when the second compartment 30 is secured in the housing unit.

The second compartment 30 preferably is cylindrical in shape and is made of or treated with a mesh material that prevents or minimizes the adhesion of mammalian cells, e.g., nylon mesh. The second compartment assumes a substantially cylindrical shape which facilitates movement of the tissue in the second compartment and reduces its entrapment therein. The volume, mesh pore size 31 and mesh material composition of the second compartment is selected based on the volume and type of the tissue to be digested. For example, if liposuctioned adipose tissue is to be introduced into the system, preferably the mesh pore openings are in the range of 200–1000 micrometers in diameter. At the ends of the second compartment are dowels 32, 32' that secure the second compartment 30 in the housing unit by fitting into corresponding annuli 15, 15' presented by the discs 13, 13' when the discs are sealably engaged with the housing unit 10. When the second compartment dowels are secured in the annuli of the discs, an airtight and watertight seal is formed. In one embodiment, an elastomeric O-ring 16 interfaces between the annuli 15, 15' and the second compartment dowels 32, 32' inserted therein to create an airtight and watertight seal. At least one second compartment dowel is hollow 32 to provide a means of communication between the interior of the second compartment 36 and the external environment and thereby provide a means for introducing tissue into the system. Preferably, such port providing access to the interior of the second compartment is self-sealing such that when a fluid or tissue source is not engaged with this port, the port is closed with an airtight and watertight seal. Even more preferably, the portion of the port engaging the external environment has a superiorly positioned opening such that fluid and tissue may be introduced into the second compartment with the assistance of gravitational forces.

Further, at least one second compartment dowel 32', when engaged with the annuli of the disc, extends beyond the exterior surface of the disc and thereby provides a means for engaging 33 a mechanism 35, 35' for rotating the second compartment within the housing unit. Such mechanism may be a manual 35 (e.g., S wrench) or automated 35' (e.g., rotor), including programmed, means for rotating the second cylinder. The second compartment also has intermittently spaced extensions 34 that radiate out from the surface of the second compartment and provide a means for mixing fluid in the main housing unit and facilitating and expediting the interaction of fluids with the tissue sample.

Preferably, the fluid port(s) 17, 32 providing direct and indirect (i.e., through the first or second compartment) access with the external environment and the housing unit are oriented with openings superiorly positioned so that solutions can be positioned above the housing unit and introduced into the system with the assistance of gravitational forces.

The housing unit has a heat source 50, preferably external to the housing unit and uniformly enveloping at least a substantial portion of the housing unit that encases the second compartment. When activated, the heat source elevates and maintains the temperature of the proteolytic enzyme solution for optimal enzymatic dissociation. For example, if the tissue to be dissociated is human tissue, a proteolytic enzymatic temperature of approximately 37° C. is achieved and maintained within the housing unit until tissue dissociation is substantially complete.

In one variation of a preferred embodiment (not shown), a fourth port communicates between the housing unit and the environment and provides a means for creating a negative pressure for filtration using a vacuum source 80. In another variation of the preferred embodiment, the fourth port providing a means for attaching a vacuum source 80 is part of or attached to the valve 40 controlling the status of the exit aperture.

At the start of the procedure, the first 20 and second 30 compartments are secured in the housing unit, the discs 13, 13' of the substantially cylindrical portion of the housing unit 11 are threadibly engaged, the exit aperture 18 is closed, and a first collection receptacle 60 is attached to the exterior lip 44 of the three-way stopcock valve. A sterile environment is thereby created inside the housing unit.

Tissue is introduced into the system through a port 32 providing communication between the external environment and the interior of the second chamber 36. The tissue may be subjected to a sedentary phase which permits a partial separation of its components. For example, if the tissue is adipose tissue resulting from a tumescent liposuction procedure, the tissue may be subjected to a sedentary phase which permits a crude separation of oil, tissue and tumescent solution in which tumescent solution is the lowest layer resulting from such separation. After such partial separation, the exit aperture 18 is opened by moving the three-way valve to an open position 40a, even more preferably, to the open position with vacuum 40c. Thus, the bottom layer, i.e., tumescent solution, is permitted to drain into the first collection receptacle 60. After the bottom layer has been drained from the housing unit, the valve is placed in the closed position 40b. If the first collection receptacle has been sufficiently filled by the volume of the effluent removed during this phase, often treated as waste, the first collection receptacle is disengaged from the valve and an empty collection receptacle is substituted.

After any potential sedentary phase, a washing solution is introduced into the first compartment 20, preferably under pressure, through a first port 17. The washing solution exudes through the ports of the first compartment 21, into the housing unit 19 and onto and into the second compartment 30 through the mesh pores 31. Preferably, the pressure under which the washing solution is introduced into the system is such that its pressure upon exit from the first compartment provides yet another means for dislodging tissue and material occluding the pores 31 of the second compartment. Also preferably, sufficient washing solution is introduced into the system such that the second compartment is substantially submerged during this washing phase. During the washing phase, the second compartment is manually or mechanically rotated or agitated by an external means 35, 35', preferably rotated, to facilitate and expedite washing the tissue in the second compartment. After the tissue is thoroughly washed, as determined by macroscopic examination or a pre-established time interval, the three-way valve 40 is placed in an open position 40a, preferably the open position with vacuum 40c. The effluent, often treated as waste, is thereby permitted to progress down the grade of the frusto-conical portion of the housing unit 12, pass through the exit aperture 18 and valve 40 configuration, and into the first collection receptacle 60 attached to the valve 40 via the threads 44 and collection receptacle threads 61. After the effluent is collected in the first receptacle 60, the valve is placed in the closed position 40b, the first collection receptacle 60 is removed, and a centrifuge-ready second collection receptacle 70 is attached to the housing unit via similar means providing for attachment of the first collection receptacle, i.e. by mating the threads 44 with the second receptacle threads 71.

A proteolytic enzyme, preferably collagenase, dispase, hyaluronidase, trypsin or combination thereof, is introduced into the housing unit, either through ports providing access to the interior of the first or second compartments 17, 32, or through a port that provides direct access to the interior of the housing unit 19 (not shown). If the proteolytic enzyme is introduced through the port providing access to the first compartment 17, the enzyme exudes through the ports of the first compartment 21, into the housing unit 19 and onto and into the second compartment 30 through the mesh pores 31 of the second compartment. Preferably, the enzyme is introduced into the system under pressure such that the pressure provides a means for dislodging tissue and material occluding the pores of the second compartment. Also preferably, sufficient enzyme is introduced into the system to substantially submerge the second compartment and the tissue therein.

During the dissociation phase, the second compartment 30 is rotated or agitated by an external means, 35 or 35', preferably rotated, to facilitate and expedite tissue dissociation. When the second compartment is rotated or agitated, the radiating extensions 34 of the second compartment gently mix the tissue, proteolytic enzyme and resulting cell suspension, and further facilitate and expedite tissue dissociation. The heat source 50 is activated and set to raise and maintain the proteolytic enzyme in the housing unit at a temperature for optimal enzymatic dissociation. For example, when adipose tissue obtained through tumescent liposuction is introduced into the system, and the enzyme is collagenase, the heat source raises the temperature of the collagenase in the system to approximately 37° C. for optimal tissue dissociation. For adipose tissue, the dissociation phase lasts approximately 20 to 60 minutes, depending on the amount of tissue and numerous other variables inherent in the use of proteolytic enzymes.

At the conclusion of the tissue dissociation phase, the heat source 50 is deactivated and a solution, e.g. media, is introduced into the housing unit through a port, i.e., the port providing access to the interior of the first compartment 17, the port providing access to the interior of the second compartment 32, or a port providing direct access to the interior of the housing unit (not shown). The solution inhibits further activity of the proteolytic enzyme and reduces the viscosity of the resulting cell suspension and thereby facilitates filtration. The second compartment continues to rotate to facilitate interaction of the solution with the cell suspension in the housing unit. The valve 40 is moved into the open position 40a, preferably the open position with vacuum 40c, and the cell suspension flows from the housing unit, down the grade of the frusto-conical portion of the housing unit 12, through the exit aperture 18 and valve 40 configuration, and into the centrifuge-ready receptacle 70. The second collection receptacle is disengaged from the valve, the top to the collection receptacle 72 is sealably engaged with the receptacle, and the cell suspension is ready for use or further processing.

Figure 3:
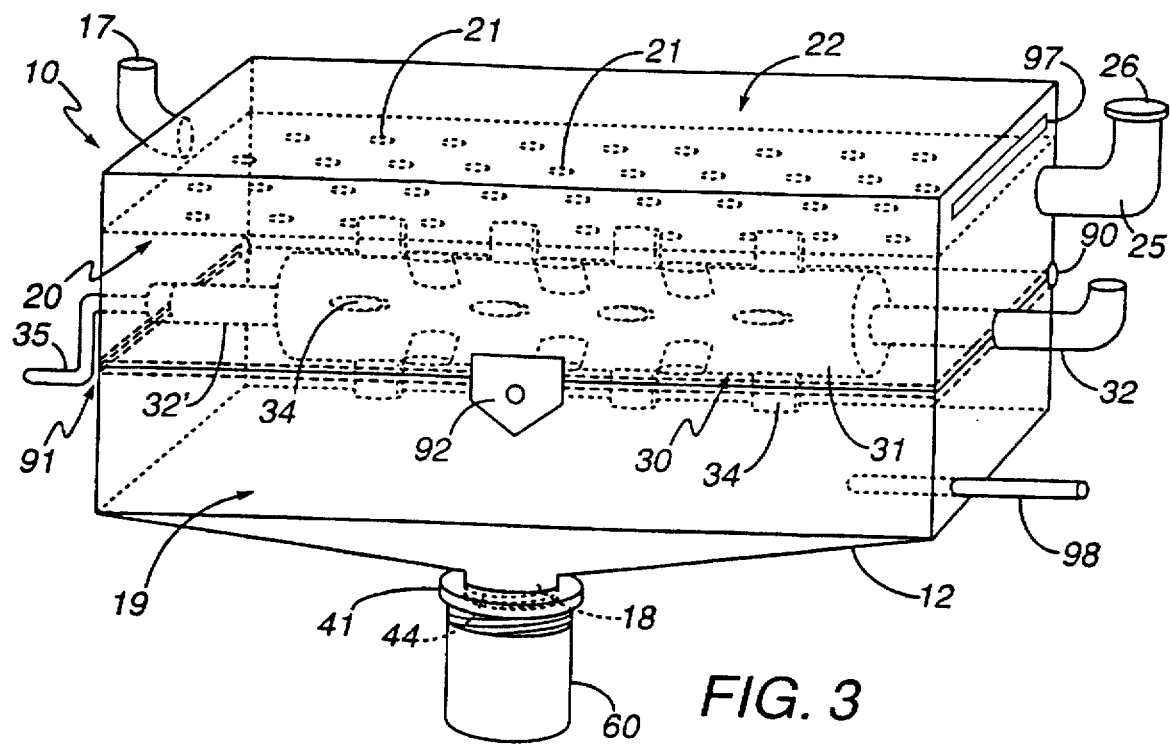
FIG. 3 is an oblique front view of a system embodying the present system.
Figure 4:
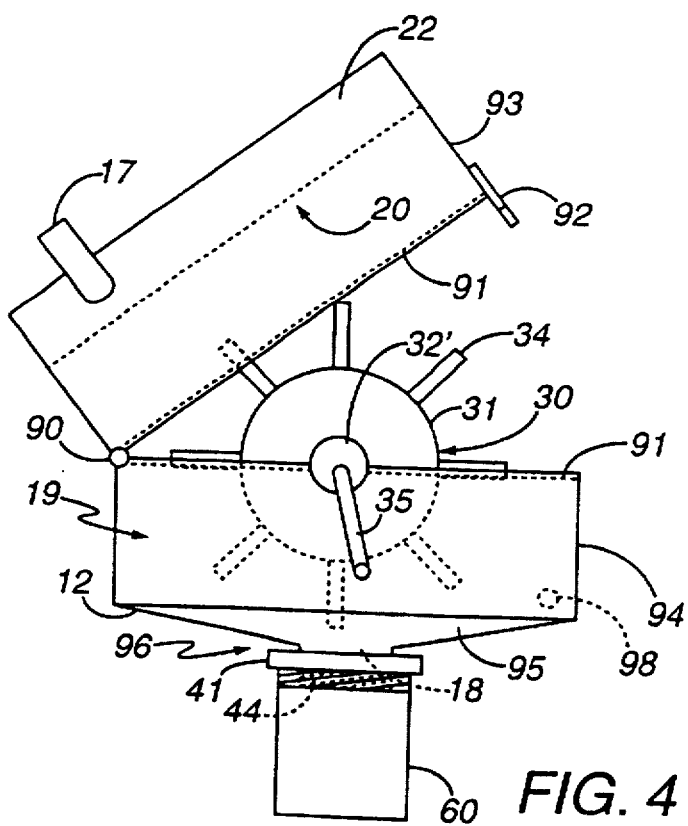
FIG. 4 is a side open view of the system embodying the present system depicted in FIG. 3.

In another embodiment of the invention, shown in FIGS. 3 and 4, the housing unit 10 has a hinging mechanism 90 to provide for easy access to the interior of the housing unit, 10 and easy cleaning and substitution of the internal components. The housing unit has a top component 93 that is attached to the lower portion of the housing unit 94 by a hinging mechanism 90, and a lower component 94 having a floor 95 that is bevelled inwardly. An airtight and watertight seal is achieved along the seam of the housing unit created when the housing unit is closed, i.e. when the lower and upper portions of the housing unit are joined, preferably by a lining of elastomeric material 91 along such seam. A locking mechanism 92, such as a lock and key mechanism or a latching mechanism, secures the housing unit in the closed position.

Figure 5A:
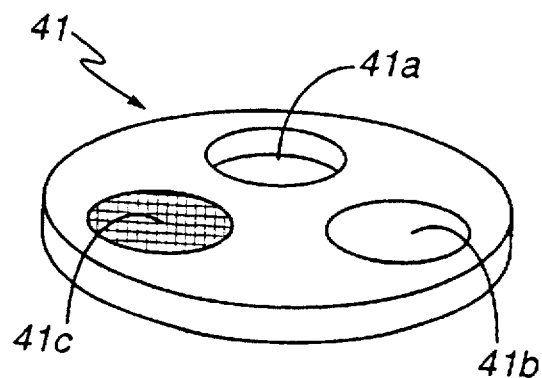
FIGS. 5a and b are obliquie views of various embodiments of a means for controlling the status of the exit aperture.
Figure 5B:
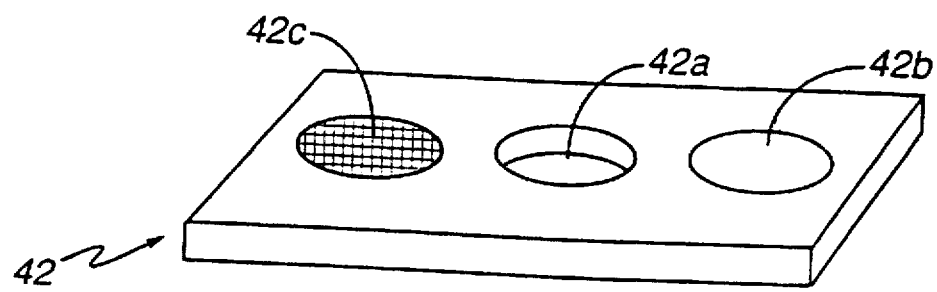

At the nadir of the bevelled floor 95 of the housing unit is an exit aperture 18. The status of the exit aperture is controlled by a disc 41 or panel 42 slidably engaged with the lower portion of the housing unit 95 and having features that provide for an open position 41a, 42a, an open position with filter 41c, 42c, or occlusion of the exit aperture 41b, 42b. See FIGS. 5a and 5b. In the open position, a hollowed portion of the disc 41a or panel 42a spans the exit aperture such that fluid communication exists between the interior of the housing unit 19 and a collection receptacle 60, 70 attached to the exterior of the housing unit. In the open position with filter, a portion of the disc or panel having a filter embedded therein 41c, 42c spans the exit aperture 18 such that fluid passing between the interior of the housing unit 19 and a receptacle 60, 70 attached to the exterior of the housing unit is thereby filtered. In one preferred embodiment, a receptacle 60, 70 attaches to a lip 96 extending from the exterior of the housing unit and encircling the exit aperture 18. In the closed position, the portion of the disc or panel spanning the exit aperture is solid 41b, 42b and an airtight and watertight seal is formed.

Within the housing unit and extending along the undersurface of the top component 93 of the housing unit is a first compartment 20. The first compartment has at least one self-sealing fluid port 17 providing communication between the interior of the first compartment 22 and the external environment. This first compartment fluid port 17 provides a means for introducing tissue processing and washing solutions into the system. The first compartment 20 also has a plurality of ports 21 providing communication between the interior of the first compartment 22 and the interior of the housing unit 19. These ports 21 are opened and closed by a shutter-like mechanism 97 controlled, manually or automatically, by a lever on the outside of the housing unit. When closed, the first compartment may serve as a storage chamber for fluids to be used in the system.

The top component of the housing unit 93 also has a filtered port 25 that provides communication between the external environment and the interior of the housing unit and permits filtered air to enter the system. It extends through the wall of the top component below the portion of the top component encasing the first compartment 20 but sufficiently high on the wall of the top component such that when fluid is introduced into the system, the fluid does not interact with the port.

The chamber of the second compartment 30 is comprised of sterilizable steel mesh which preferably is treated with a teflon coating to reduce the adherence of tissue cells to the second compartment. Preferably, the second compartment is substantially cylindrical in shape and has dowels for engaging and securing the second compartment in the housing unit. Annuli 15, 15', which are embedded in and bisected by the hinged top 93 and bottom 94 components of the housing unit, provide a means for securing the second compartment 30 in the housing unit in an airtight and watertight fashion, when the housing unit is closed, i.e., when the top 93 and bottom 94 components are fitted onto each other, and sealed shut. Preferably, these annuli are lined with an elastomeric material. The dowels 32, 32' extending from the extreme ends of the second compartment fit in the annuli 15, 15' of the housing unit. At least one dowel 32' extends through the annuli 15' of the housing unit and beyond the exterior surface of the housing unit, and provides a means for engaging a mechanism 35, 35' to agitate or rotate the second compartment. Further, at least one dowel is hollow 32 and the entrance port it acts as is self-sealing, and extends through the annuli 15 of the housing unit and beyond the exterior surface of the housing unit and thereby provides a port for inserting tissue samples, and possibly solutions, into the second compartment. In one preferred embodiment, both dowels are hollow and act as a port and extend beyond the exterior of the housing unit and provide a means for engaging a mechanism for rotating or agitating the second compartment. The second compartment is agitated or rotated manually or by an automated, e.g., programmed, power source, 35, 35'.

The second compartment also has extensions 34 attached to the exterior surface of the second compartment that provide a means for mixing fluid in the housing unit. Preferably, the extensions are intermittently spaced and perpendicular to provide minimal interference with access and egress of effluent from the interior of the second compartment.

A probe 98 may also be inserted into the lower portion of the housing unit to monitor and possibly measure reactions and conditions within the main housing unit, e.g. tissue dissociation and temperature. Such probe may provide input to automated portions of the system.

At the start of the process, the dowels of the second compartment 32, 32' are nested in the annuli 15, 15' of the housing unit, the housing unit is sealed shut, the ports providing communication between the interior of the first compartment and the interior of the housing unit 21 are closed, the disc 41 or panel 42 controlling the status of the exit aperture is placed in the closed position, and a first collection receptacle 60 is sealably engaged with the exterior of the housing unit. Washing solution is inserted into the first compartment 20 through the first port 17 and may be stored therein until the start of the process. A tissue sample is inserted into the second compartment 30 via the port providing access thereto 32. The plurality of ports 21 providing access between the interior of the first compartment and the housing unit are opened by adjustment of the mechanism that controls their status, 97, and washing solution, under gravitational forces, descends from the first compartment 20 into the interior of the housing unit 19 and onto and into the second compartment through the pores of the cylinder mesh 31 and interacts with the tissue in the second compartment. Preferably, sufficient fluid is introduced into the system to substantially submerge the tissue sample.

The second compartment is agitated by the means provided therefore, 35, 35' and the tissue is thereby washed. After sufficient washing solution has been introduced into the housing unit, the ports providing communication between the interior of the housing unit and the interior of the first compartment 21 are closed. The disc 41 or panel 42 is placed in the open position 41a, 42a and effluent travels down the bevelled floor 95 of the housing unit, through the exit aperture and into the first collection receptacle. The disc or panel is placed in the closed position 41b, 42b, the first receptacle 60 is disengaged from the housing unit and a centrifuge-ready collection receptacle 70 is attached to the housing unit.

In an alternative embodiment, after the washing phase, the ports providing communication between the interior of the housing unit and the interior of the first compartment 21 are kept open and washing solution continues to descend onto and into the second compartment 30 and interact with the tissue therein while the disc 41 or panel 42 is placed in the open position and waste effluent travels down the bevelled floor 95 of the housing unit, through the exit aperture and into the first collection receptacle 60, and thereby provides a rinse step to the process. At the conclusion of the rinse step, the ports providing communication between the interior of the housing unit and the interior of the first compartment 21 are closed, the disc 41 or panel 42 is placed in the closed position, the first receptacle 60 is disengaged from the housing unit and a centrifuge-ready collection receptacle is sealably engaged with the housing unit.

A proteolytic enzyme solution is inserted into the second compartment via the port providing access thereto. Preferably, sufficient proteolytic enzyme solution is introduced into the system to submerge the tissue sample in the second compartment. The second compartment is agitated and the extensions of the second compartment 34 mix the fluid in the housing unit and thereby facilitate and accelerate tissue dissociation. Further, the heat source 50 (not shown in FIGS. 3 and 4) is engaged to bring the proteolytic enzyme in the housing unit to the optimal temperature for tissue dissociation. After conclusion of the tissue dissociation phase, as determined by macroscopic examination or a pre-determined timed interval, the disc or panel is moved to the open position 41a, 42a and the cell suspension resulting from tissue dissociation flows from the housing unit, through the exit aperture 18, and into the centrifuge-ready receptacle 70. Alternatively, the disc or panel is moved to the filter position and the cell suspension resulting from tissue dissociation flows from the housing unit, through the exit aperture 18, through the filter 41c, 42c and into the centrifuge-ready receptacle 70. The receptacle is disengaged from the main housing unit and the cap of the receptacle is sealably engaged with the receptacle to maintain the sterile environment therein, and the cell suspension is ready for further processing or use.

It will be obvious to one skilled in the art that it is possible to combine different features of the different embodiments described above to practice the present invention.

What is claimed is:

1. A system for dissociating tissue comprising:
   a. a housing unit having a means of accessing the interior of said housing unit and having a downwardly inclined floor wherein an aperture exists at the nadir of said inclined floor;
   b. a first compartment having a plurality of fluid communicating means between the interior of said first compartment and the interior of said housing unit;
   c. a first inlet port that provides communication between the exterior environment and said interior of said first compartment and thereby provides a means for introducing solutions into said interior of said first compartment;
   d. a second compartment having pores providing for fluid communication between the interior of said second compartment and said interior of said housing unit and a means for reversibly securing said second compartment in said housing unit while permitting said second compartment to be rotated or agitated;
   e. a second inlet port for introducing a tissue sample into said second compartment;
   f. a third inlet port wherein said third inlet port has a filter and provides a means for filtered air to enter said housing unit;
   g. a means for agitating or rotating said second compartment in said housing unit;
   h. a means for controlling the exit of effluent through said aperture;
   i. a first receptacle sealably engaging said housing unit; and
   j. a second receptacle for collecting a cell suspension wherein said second receptacle is centrifuge-ready and sealably engages said housing unit.

2. A system for dissociating tissue according to claim 1 further comprising a heat source.

3. A system for dissociating tissue according to claim 1 further comprising a vacuum source.

4. A system for dissociating tissue according to claim 1 wherein said first compartment has a reversible means for occluding said plurality of fluid communicating means between said interior of said first compartment and said interior of said housing unit.

5. A system for dissociating tissue according to claim 1 wherein said plurality of fluid communicating means between said interior of said first compartment and said interior of said housing unit are located on the surface of the portion of said first compartment facing said second compartment housed within said housing unit.

6. A system for dissociating tissue according to claim 1 wherein said second compartment is substantially cylindrical in shape.

7. A system for dissociating tissue according to claim 1 wherein said second compartment is substantially cylindrical in shape and said pores of said second compartment are between 50 and 2000 microns.

8. A system for dissociating tissue according to claim 1 wherein said second compartment has extensions radiating out from the exterior surface of said second compartment to facilitate the interaction of materials in said housing unit.

9. A system for dissociating tissue according to claim 1 wherein said means for controlling the exit of effluent through said aperture in the floor of said housing unit is one of a group consisting of:
   a. a valve having an open position and closed position;
   b. a three-way valve having an open position, an open position with vacuum and a closed position;
   c. a valve having an open position, an open position with vacuum, an open position with filter, an open position with filter and vacuum, and a closed position;
   d. a panel, slidably and sealingly engaged with said housing unit and having an open position and closed position;
   e. a panel, slidably and sealingly engaged with said housing unit and having an open position, an open position with filter, and closed position;
   f. a disc slidably and sealingly engaged with said housing unit and having an open position and a closed position; or
   g. a disc slidably and sealingly engaged with said housing unit and having an open position, an open position with filter, and a closed position.

10. A system for dissociating adipose tissue comprising:
    a. a housing unit having a means of accessing the interior of said housing unit and having an inclined floor wherein an aperture exists at the nadir of said inclined floor;
    b. a first compartment having a plurality of fluid communicating means between the interior of said first compartment and said interior of said housing unit;
    c. a first inlet port that provides communication between the exterior environment and said interior of said first compartment and thereby provides a means for introducing solutions into said interior of said first compartment;
    d. a second compartment having pores providing for fluid communication between the interior of said second compartment and said interior of said housing unit, and a means for reversibly securing said second compartment in said housing unit while permitting said second compartment to be rotated or agitated;
    e. a second inlet port for introducing a tissue sample into said second compartment;
    f. a third inlet port wherein said third inlet port has a filter and provides a means for filtered air to enter said housing unit;
    g. a means for agitating or rotating said second compartment in said housing unit;
    h. a means for controlling the exit of effluent through said aperture in said floor of said housing unit;
    i. a heat source;
    j. a vacuum source;
    k. a first receptacle capable of sealably engaging with said housing unit; and
    l. a second receptacle for collecting a resulting cell suspension wherein said second receptacle is centrifuge-ready and sealably engages said housing unit.

11. A method for dissociating tissue comprising:
    a. providing a system for dissociating tissue having a housing unit having a first compartment and second compartment located therein wherein said first compartment is superiorly positioned relative to said second compartment and said first compartment has a plurality of fluid communicating means between the interior of said first compartment and the interior of said housing unit, said second compartment having pores providing for fluid communication between the interior of said second compartment and said interior of the housing unit, a first inlet port that provides communication between the exterior environment and said interior of said first compartment and provides a means for introducing solutions into said interior of said first compartment, a second inlet port for introducing tissue into said second compartment, a third inlet port wherein said port has a filter and provides a means for filtered air to enter said housing unit, said second compartment having a means for engaging a rotating or agitating mechanism, a means for rotating or agitating said second compartment, a heat source, said housing unit having a downwardly inclined floor wherein an aperture exists at the nadir of said inclined floor, a means for controlling the exit of effluent through said aperture, a first receptacle sealably engaging said housing unit, and a second receptacle wherein said second receptacle is centrifuge-ready and sealably engages said housing unit;

b. inserting tissue to be dissociated into said second compartment via said second inlet port;

c. inserting a washing solution into said first compartment via said first inlet port;

d. permitting said washing solution to descend through said plurality of fluid communicating means between said interior of said first compartment and said interior of said housing unit, through said pores providing for fluid communication between said interior of said second compartment and said interior of said housing unit, and into said second compartment where it interacts with the tissue inserted therein;

e. placing said means for controlling the exit of effluent through said aperture in an open position such that said effluent exits the housing unit and is collected in said first receptacle;

f. placing said means for controlling the exit of effluent through said aperture in a closed position and disengaging said first receptacle and sealably engaging said second receptacle;

g. inserting a proteolytic enzyme solution into said housing unit;

h. heating said proteolytic enzyme solution using said heat source while agitating or rotating said second compartment within said housing unit using said means for agitating or rotating said second compartment and thereby facilitating tissue dissociation;

i. placing said means for controlling the exit of effluent through said aperture in an open position such that effluent exits said housing unit and is collected in said second receptacle;

j. collecting the cell suspension resulting from tissue dissociation in said second receptacle; and k. sealing said second receptacle closed.

12. A method for dissociating tissue according to claim 11 wherein said washing solution is introduced into the system under pressure such that the pressure of said washing solution when it interacts with said second compartment dislodges materials occluding said pores of said second compartment.

13. A method for dissociating tissue according to claim 11 further comprising a sedentary step wherein components of said tissue are permitted to separate based on their density properties and placing said means for controlling the exit of effluent through said aperture in an open position such that effluent exits said housing unit and is collected in said first receptacle, wherein said sedentary step is performed before permitting said washing solution to descend through said plurality of fluid communicating means between said interior of said first compartment and said interior of said housing unit.

14. A method for dissociating tissue according to claim 11 further comprising:

a. subjecting said tissue to a sedentary step wherein components of said tissue are permitted to separate based on density properties; and b. placing said means for controlling the exit of effluent through said aperture in an open position such that effluent exits the housing unit and is collected in said first receptacle, wherein said sedentary step is performed before permitting said washing solution to descend through said plurality of fluid communicating means between said interior of said first compartment and said interior of said housing unit; and c. inserting a solution that inhibits proteolytic enzyme activity into said housing unit while agitating or rotating said second compartment within said housing unit, wherein said insertion of said solution is performed before placing said means for controlling the exit of effluent through said aperture in an open position such that effluent exits said housing unit and is collected in said second receptacle.

15. A method for dissociating tissue according to claim 11 further comprising agitating or rotating said second compartment while said washing solution is inserted into said system for dissociating tissue and while said proteolytic enzyme solution is inserted into said system.

16. A method for dissociating tissue according to claim 11 wherein said washing solution and said proteolytic enzyme solution are introduced into said system under pressure such that the pressure of said washing solution and said proteolytic enzyme solution dislodges material occluding said pores of said second compartment when said washing solution and said proteolytic enzyme solution interact with said second compartment.

17. A method for dissociating tissue according to claim 11 further comprising inserting a solution that inhibits proteolytic enzyme solution activity into said housing unit while agitating or rotating said second compartment within said housing unit before placing said means for controlling the exit of effluent through said aperture in an open position such that effluent exits said housing unit and is collected in said second receptacle.

18. A method for dissociating tissue according to claim 11 further comprising a step of permitting said washing solution to descend through said plurality of fluid communicating means between said interior of said first compartment and said interior of said housing unit, through said pores providing for fluid communication between said interior of said second compartment and said interior of said housing unit, and into said second compartment where it interacts with the tissue inserted therein while said means for controlling the exit of effluent through said aperture in an open position such that said effluent exits the housing unit and is collected in said first receptacle, wherein said step is performed immediately before placing said means for controlling the exit of effluent through said aperture in a closed position and disengaging said first receptacle and sealably engaging said second receptacle.

19. A method for dissociating tissue according to claim 11 wherein said tissue to be dissociated and introduced into said second compartment is adipose tissue.

20. A method for dissociating tissue according to claim 11 wherein said tissue to be dissociated and introduced into said second compartment is adipose tissue harvested by a liposuction procedure using tumescent solution and further comprising the steps of:

a. subjecting said tissue to a sedentary step wherein components of said tissue are permitted to separate based on density properties; and b. placing said means for controlling the exit of effluent through said aperture in an open position such that effluent exits said housing unit and is collected in said first receptacle, wherein said sedentary step is performed before permitting said washing solution to descend through said plurality of fluid communicating means between said interior of said first compartment and said interior of said housing unit; and c. inserting a solution that inhibits proteolytic enzyme solution activity into said housing unit while agitating or rotating said second compartment within said housing unit, wherein said inserting of said solution is performed before placing said means for controlling the exit of effluent through said aperture in an open position such that effluent exits said housing unit and is collected in said second receptacle.

* * * * *